United States Patent [19]

Diamond

[11] 3,985,788

[45] Oct. 12, 1976

[54] PHENYL PROPIONIC ACIDS AND DERIVATIVES THEREOF
[75] Inventor: Julius Diamond, Lafayette Hills, Pa.
[73] Assignee: William H. Rorer, Inc., Fort Washington, Pa.
[22] Filed: Oct. 4, 1973
[21] Appl. No.: 403,516

Related U.S. Application Data
[63] Continuation of Ser. No. 164,822, July 21, 1971, abandoned.

[52] U.S. Cl. ............................ 260/469; 260/448 R; 260/465 D; 260/470; 260/471 R; 260/501.16; 260/515 A
[51] Int. Cl.² .................. C07C 63/33; C07C 69/76
[58] Field of Search ............ 260/515 A, 471 R, 470, 260/465 D, 469, 501.16, 448 R

[56] References Cited
UNITED STATES PATENTS

| | | | |
|---|---|---|---|
| 3,435,075 | 3/1969 | Glamkowski et al. | 260/515 |
| 3,852,323 | 12/1974 | Diamond et al. | 260/465 |

*Primary Examiner*—Jane S. Myers
*Attorney, Agent, or Firm*—Erich M. H. Radde

[57] ABSTRACT

Novel α-halo-β-(4-cyclohexylphenyl)propionic acids and their salts and esters are described. Therapeutic compositions containing same and a method of treating inflammation by their administration are also disclosed.

21 Claims, No Drawings

PHENYL PROPIONIC ACIDS AND DERIVATIVES THEREOF

The present application is a continuation of application Ser. No. 164,822, filed July 21, 1971, now abandoned.

SUMMARY OF THE INVENTION

This invention describes novel α-substituted p-cycloalkylphenylpropionic acids and their derivatives and their use in therapeutic compositions. In addition, this invention relates to the preparation of α-substituted p-cycloalkylphenylpropionic acids. When the compounds of this invention are administered to mammals, they afford significant treatment of inflammation and associated pain and fever.

They further provide analgesic and antipyretic methods for the relief and treatment of pain and fever associated with inflammation.

BACKGROUND OF THE INVENTION

There has been continued efforts in research to develop drugs which would significantly inhibit the development of inflammation and relieve the pain and fever associated with it. Much of these efforts have been carried on in the field of steroids. While many of these compounds have been effective, they have had the drawback of causing many side effects.

I have unexpectedly found that α-halo-p-cyclohexylphenyl-propionic acid compounds and their derivatives have valuable pharmacologic properties.

I have found that α-halo-p-cyclohexylphenylpropionic acid compounds and their derivatives possess useful anti-inflammatory, analgesic and anti-pyretic properties.

I have also found a series of anti-inflammatory compounds which are non-steroidal.

I have further found that these α-halo-p-cyclohexylphenylpropionic acid compounds and their derivatives are novel.

I have also found that the compounds of this invention are useful in effectively providing a method for the inhibition of inflammation and the treatment of associated pain and fever.

I have still further found an entirely new class of anti-inflammatory, analgesic and antipyretic pharmaceutical compositions containing the α-halo-p-cyclohexylphenylpropionic acids and derivatives of this invention as active ingredient.

I have again found a convenient method for synthesizing these compounds.

DESCRIPTION AND PREFERRED EMBODIMENT

This invention comprises a class of novel chemical compounds which contain a cyclohexyl substituted phenyl radical which is attached to an α-halo propionic acid in the β-position. This invention further comprises derivatives of said propionic acids and the method of preparing the same.

This invention also describes a new method of treating inflammation and associated pain and fever as well as novel therapeutic compositions.

The compounds of this invention are represented by the following formula I:

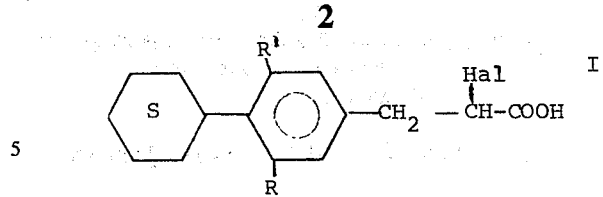

where:
R
  is halo,
  nitro,
  loweralkylsulfonyl
  haloloweralkyl or
  cyano;
R'
  is hydrogen,
  chloro,
  bromo or
  nitro;
Hal
  is halo, Included within the scope of this invention are the racemic mixtures as well as the dextro and levorotatory isomers thereof.

Another special embodiment which describes novel compounds that are effective in inhibiting inflammation and the treatment of pain and fever associated with inflammation as well as having analgesic and antipyretic effectiveness for the relief and treatment of pain and fever or symptomatically related to an inflammation indication are described by formula II.

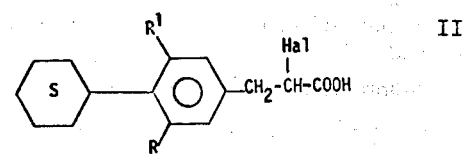

where:
R
  is chloro,
  bromo,
  nitro,
  methylsulfonyl,
  trifluoromethyl or
  cyano;
R'
  is hydrogen,
  chloro,
  bromo or
  nitro; and
Hal is
  fluoro,
  chloro or
  bromo Those compounds where Hal is chloro are even more preferred.

Included within the scope of this further special embodiment are the racemic mixtures as well as the dextro and levorotatory isomers thereof.

In the descriptive portions of this invention, the following definitions apply:

The term lower alkyl refers to a lower alkyl hydrocarbon group containing from 1 to about 6 carbon atoms which may be straight chained or branched.

Lower alkoxy signifies an alkoxy group containing from 1 to about 6 carbon atoms which may be straight chaired or branched.

The preferred alkali or alkaline earth metals are sodium, potassium, calcium and magnesium.

Representative compounds are

α-fluoro-β-(3-chloro-4-cyclohexylphenyl)propionic acid
α,3-difluoro-β-(4-cyclohexylphenyl)propionic acid
α-fluoro-β-(3-bromo-4-cyclohexylphenyl)propionic acid
α-fluoro-β-(3-nitro-4-cyclohexylphenyl)propionic acid
α-fluoro-β-(3-methylsulfonyl-4-cyclohexylphenyl)-propionic acid
α-fluoro-β-(3-trifluoromethyl-4-cyclohexylphenyl)-propionic acid
α-fluoro-β-(3-cyano-4-cyclohexylphenyl)propionic acid
α-chloro-β-(3-fluoro-4-cyclohexylphenyl)propionic acid
α,3-dichloro-β-(4-cyclohexylphenyl)propionic acid
α-chloro-β-(3-bromo-4-cyclohexylphenyl)propionic acid
α-chloro-β-(3-nitro-4-cyclohexylphenyl)propionic acid
α-chloro-β-(3-methylsulfonyl-4-cyclohexylphenyl)-propionic acid
α-chloro-β-(3-trifluoromethyl-4-cyclohexylphenyl)-propionic acid
α-chloro-β-(3-cyano-4-cyclohexylphenyl)propionic acid
α-bromo-β-(3-fluoro-4-cyclohexylphenyl)propionic acid
α-bormo-β-(3-chloro-4-cyclohexylphenyl)propionic acid
α,3-dibromo-β-(4-cyclohexylphenyl)propionic acid
α-bromo-β-(3-nitro-4-cyclohexylphenyl)propionic acid
α-bromo-β-(3-methylsulfonyl-4-cyclohexylphenyl)-propionic acid
α-bromo-β-(3-trifluoromethyl-4-cyclohexylphenyl)-propionic acid
α-bromo-β-(3-cyano-4-cyclohexylphenyl)propionic acid
d   α-fluoro-β-(3-chloro-4-cyclohexylphenyl)propionic acid
l   α-fluoro-β-(3-chloro-4-cyclohexylphenyl)propionic acid
d   α,3-dichloro-β-(4-cyclohexylphenyl)propionic acid
l   α,3-dichloro-β-(4-cyclohexylphenyl)propionic acid
d   α-bromo-β-(3-chloro-4-cyclohexylphenyl)propionic acid
l   α-bromo-β-(3-chloro-4-cyclohexylphenyl)propionic acid When a substituted α-(p-cycloalkylphenyl)lactate is reacted with a phosphorus trihalide, phosphorus pentahalide, phosphorus oxyhalide, sulfurylhalide, thionyl halide, or sulfuric halide the corresponding α-halo-β-(p-cycloalkylphenyl)propionate is prepared.

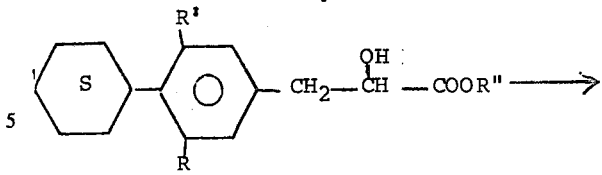

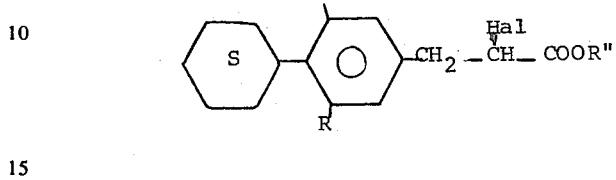

where
R' is lower alkyl;
Hal is fluoro, chloro, bromo or iodo.

The corresponding α-halopropionic acid may be prepared by heating the ester with acetic acid containing the corresponding hydrogen halide.

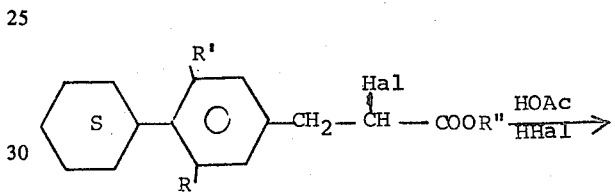

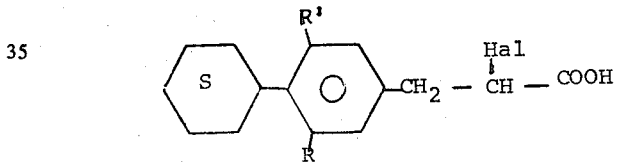

where:
R'' is lower alkyl.

The substituted α-fluoro-β-(p-cycloalkylphenyl)propionic acid derivatives may also be obtained from the corresponding α-iodo, α-bromo or α-chloro-β-(p-cycloalkylphenyl)propionic acid derivatives by reaction with potassium fluoride at about 130°–200°C.

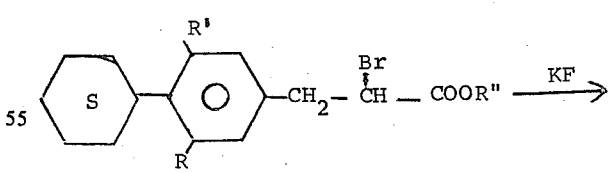

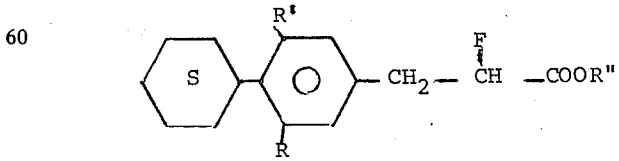

The corresponding acid salts, esters and amides of the foregoing α-halopropionic acids may be prepared according to the previously described procedures on the replacement of the hydroxyl group with halo may be carried out on the desired acid salt, ester or amide.

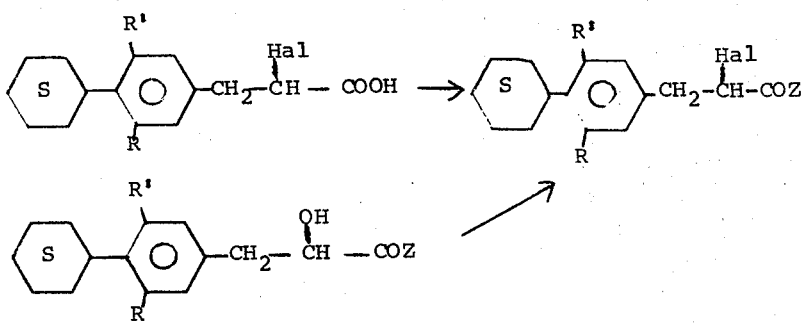

These and other equivalent methods for the preparation of the acid, ester, amide, alcohols and derivatives of the instant products will be apparent to those having ordinary skill in the art.

When the β-carbon is substituted with hydrogen, the products of this invention are obtained as racemic mixtures of their dextro and levorotatory isomers since the α-carbon is asymmetric. These isomers may be separated by fractional crystallization and resolved into dextro and levorotatory optical isomers by conventional methods.

One method of resolution that may be employed is combining the racemic compound with an optically active compound by salt formation, ester formation, or amide formation to form two isomeric products. If the instant acids are added to an optically active base, then two isomeric salts are produced which possess different properties and different solubilities and can be separated by fractional crystallization. When the salts have been completely separated by repeated crystallization, the base is split off by acid hydrolysis and the pure d and l acids are obtained. Preferably, a cycloalkylphenyl-α-substituted propionic acid is reacted in alcoholic or acetone solution with an equivalent amount of the optically active primary, secondary or tertiary amine such as cinchonidine, cinchonine, quinine, ephedrine, α-methylbenzylamine, sec-butylamine, sec-amylamine, etc. The isomeric amine salts produced thereby, are separated by fractional crystallization and each optically active salt is hydrolyzed with dilute mineral acid to produce the dextro or levo form of the cycloalkyl-phenyl-α-substituted propionic acid.

Still alternatively, a cycloalkylphenyl-α-substituted propionate may be reacted with an optically active alcohol such as l-menthol or d-borneol, or l-α-methyl-benzylalcohol, to produce a mixture of isomeric cycloalkylphenyl-α-substituted propionate esters which may be separated by fractional crystallization. Each optically active ester may be hydrolyzed with mineral acid or alkali to its respective optically active acid. The optically active acids can also be recovered from the α-methylbenzyl esters by hydrogenolysis in the presence of palladium. In this manner the α-halo isomers may be prepared.

I have found that the compounds of this invention exercise a useful degree of anti-inflammatory activity in mammals and are effective in the treatment of associated pain and fever and in like conditions which are responsive to treatment with anti-inflammatory agents.

In general, the compounds of this invention are indicated for a wide variety of mammalian conditions where the symptoms of inflammation and associated fever and pain are manifested. Exemplary of such conditions are: rheumatic diseases such as rheumatoid arthritis, osteoarthritis and other degenerative joint diseases; soft-tissue rheumatism such as tendinitis; muscular rheumatism such as sciatica; pain and inflammation associated with dental surgery and similar human and veterinary disease conditions exhibiting the foregoing symptoms requiring the use of an anti-inflammatory, analgesic and/or antipyretic agent.

For these purposes, the compounds of this invention are normally administered orally, topically, parenterally or rectally. Orally, these may be administered in tablets, capsules, suspensions or syrups; the optimum dosage, of course, depending on the particular compound being used and the type and severity of the condition being treated. In any specific case the appropriate dosage selected will further depend on factors of the patient which may influence response to the drug; for example, general health, age, weight, etc. Although the optimum quantities of the compounds of this invention to be used in such manner will depend on the compound employed and the particular type of disease condition treated, oral dose levels of preferred compounds when administered to a mammal in dosages of 0.5 to 100 milligrams per kilogram of body weight per day are particularly useful. The preferred range is 0.5 to 15 mg/Kg. Comparative dosages may be used in topical, parenteral or rectal administration.

Dosage forms may be prepared according to any method known to the art for the manufacture of pharmaceutical compositions and such compositions may contain one or more agents; for example, sweetening agents, flavoring agents, coloring agent preserving agents, etc. Further, the active p-cycloalkylphenyl-α-substituted propionic acids or their derivatives may be administered alone or in admixture with antacids such as sodium bicarbonate, magnesium carbonate, magnesium hydroxide, aluminum hydroxide, magnesium silicate, etc., and non-toxic pharmaceutically acceptable excipients. Such excipients may be, for example, inert diluents such as calcium carbonate, lactose, etc., granulating and disintegrating agents; for example maize startch, alginic acid, etc., lubricating agents; for example, magnesium stearate, talc, etc., binding agents; for example, starch gelatin, etc., suspending agents; for example, methylcellulose, vegetable oil, etc., dispersing agents; for example, lecithin, etc., thickening agents; for example, beeswax, hard paraffin, etc., emulsifying agents; for example, naturally occurring gums, etc., and non-irritating excipient; for example, cocoa butter and polyethylene glycols.

Various tests in animals can be carried out to show the ability of the p-cycloalkylphenyl-α-substituted propionic acids and derivatives of this invention to exhibit reactions that can be correlated with anti-inflammatory activity in humans. One such test is the carrageenan paw edema test, which shows the ability of the instant compounds to inhibit edema induced by injection of an inflammatory agent such as carrageenan into the tissues of the paw of a rat against non-inflamed controls. This carrageenan testing method is known to correlate well with anti-inflammatory activity in humans and is a standard test used to determine anti-inflammatory activity. This correlation can be shown by the activities of compounds known to be clinically active including such as aspirin, phenylbutazone, cortisone, hydrocortisone, indomethacin and prednisolone. In view of the results of this test, the p-cycloalkylphenyl-α-substituted propionic acids and derivatives can be considered to be active anti-inflammatory agents.

One method for measuring the pain and threshold of the p-cycloalkylphenyl-α-substituted propionic acids and derivatives is the Randall-Selitto test. Analgesic activity is shown by antinocieceptive testing of the inflammed foot of rats and a measurement of their pain response.

Anti-pyretic assay is carried out by yeast-induced fever tests of subcutaneously injected rats. The measurement of rectal temperatures is carried out to determine the response by the test compounds.

In view of the results of the above tests, the p-cycloalkylphenyl-α-substituted propionic acids and derivatives of this invention are considered to have valuable analgesic and antipyretic properties.

Other tests which can be correlated to show significant activites are the "phenylquinone writhing" test for analgesia, "polyarthritis in rats" and "ultra-violet erythema in guinea pigs".

The following are detailed examples which show the preparation of the compounds of this invention. They are to be construed as illustrations of said compounds and not as limitations thereof.

EXAMPLE 1

Ethyl α-chloro-β-(3-chloro-4-cyclohexylphenyl)propionate

A mixture of 232 g. (0.747 mole) of ethyl β-(3-chloro-4-cyclohexylphenyl)lactate is stirred with 106.67 g. (0.895 mole) of thionyl chloride at room temperature for 24 hours and then heated to reflux for 6 hours. The cold reaction mixture is poured into 1125 ml. of ice-cold water with stirring. The mixture is extracted with 800 ml. of ether. The ethereal solution is washed with 450 ml. of cold saturated sodium hydrocarbonate solution followed by washing twice, each time with 250 ml. of cold water. The ethereal solution is dried over anhydrous sodium sulfate and filtered. The solvent is removed in vacuo to obtain ethyl α-chloro-β-(3-chloro-4-cyclohexylphenyl)propionate.

EXAMPLE 2

Ethyl α-chloro-β-(3,5-dichloro-4-cyclohexylphenyl)propionate

To a mixture of 23.8 g. (0.077 moles) of ethyl β-(3,5-dichloro-4-cyclohexylphenyl)propionate in 35 ml. of benzene is added 19.2 g. (0.092 moles) of phosphorous pentachloride in small portions over 1½ hours. The mixture is stirred for 20 hours and then poured into an ice-cold mixture. The reaction mixture is extracted with petroleum ether which is then washed with cold 10% sodium bicarbonate solution followed by water. On drying, the mixture is evaporated in vacuo to ethyl α-chloro-β-(3,5-dichloro-4-cyclohexylphenyl)propionate.

EXAMPLE 3

When the procedures of Examples 1 and 2 are followed but ethyl β-(3-chloro-4-cyclohexylphenyl)lactate is replaced by the dl, d and l lactates of this invention, then the corresponding dl, d and l α-chloro-propionate products are prepared. A representative list of the compounds obtained is shown in Table I, below.

TABLE I ethyl α-chloro-β-(3,5-ditrifluoromethyl-4-cyclohexylphenyl)propionate
ethyl α-chloro-β-(3-chloro-4-cyclohexylphenyl)propionate
ethyl α-chloro-β-(3-cyano-4-cyclohexylphenyl)propionate
benzyl α-chloro-β-(3-cyano-4-cyclohexylphenyl)propionate
ethyl α-chloro-β-(3-trifluoromethyl-4-cyclohexylphenyl)propionate
ethyl α-chloro-β-(3-fluoro-4-cyclohexylphenyl)propionate
ethyl α-chloro-β-(3-bromo-4-cyclohexylphenyl)propionate
ethyl α-chloro-β-(3-nitro-5-fluoro-4-cyclohexylphenyl)propionate
ethyl α-chloro-β-(3-chloro-5-nitro-4-cyclohexylphenyl)propionate
ethyl α-chloro-β-(3-nitro-5-bromo-4-cyclohexylphenyl)propionate
ethyl α-chloro-β-(3-nitro-5-trifluoromethyl-4-cyclohexylphenyl)propionate
ethyl α-chloro-β-(3-chloro-5-cyano-4-cyclohexylphenyl)propionate
benzyl α-chloro-β-(3-chloro-5-cyano-4-cyclohexylphenyl)propionate
ethyl α-chloro-β-(3-chloro-5-fluoro-4-cyclohexylphenyl)propionate
ethyl α-chloro-β-(3-chloro-5-trifluoromethyl-4-cyclohexylphenyl)propionate
ethyl α-chloro-β-(3-chloro-5-methylsulfonyl-4-cyclohexylphenyl)propionate
ethyl α-chloro-β-(3-chloro-5-iodo-4-cyclohexylphenyl)propionate
ethyl α-chloro-β-(3-chloro-5-fluoro-4-cyclohexylphenyl)propionate
ethyl α-chloro-β-(3-chloro-5-bromo-4-cyclohexylphenyl)propionate
ethyl α-chloro-β-(3,5-difluoro-4-cyclohexylphenyl)propionate
ethyl α-chloro-β-(3-cyano-5-fluoro-4-cyclohexylphenyl)propionate
benzyl α-chloro-β-(3-cyano-5-fluoro-4-cyclohexylphenyl)propionate
ethyl α-chloro-β-(3-bromo-5-fluoro-4-cyclohexylphenyl)propionate
ethyl α-chloro-β-(3-cyano-5-bromo-4-cyclohexylphenyl)propionate
benzyl α-chloro-β-(3-cyano-5-bromo-4-cyclohexylphenyl)propionate ethyl α-chloro-β-(3,5-dibromo-4-cyclohexylphenyl)-propionate
ethyl α-chloro-β-(3-fluoro-5-trifluoromethyl-4-cyclohexylphenyl)propionate
ethyl α-chloro-β-(3-cyano-5-trifluoromethyl-4-cyclohexylphenyl)propionate
ethyl α-chloro-β-(3-bromo-5-trifluoromethyl-4-cyclohexylphenyl)propionate
ethyl α-chloro-β-(3,5-ditrifluoromethyl-4-cyclohexylphenyl)propionate
methyl α-chloro-β-(3-chloro-4-cyclohexylphenyl)-propionate
methyl α-chloro-β-(3,5-dichloro-4-cyclohexylphenyl)propionate
propyl α-chloro-β-(3-chloro-4-cyclohexylphenyl)-propionate
propyl α-chloro-β-(3,5-dichloro-4-cyclohexylphenyl)propionate
i-propyl α-chloro-β-(3-chloro-4-cyclohexylphenyl)-propionate
i-propyl α-chloro-β-(3,5-dichloro-4-cyclohexylphenyl)propionate
t-butyl α-chloro-β-(3-chloro-4-cyclohexylphenyl)-propionate
t-butyl α-chloro-β-(3,5-dichloro-4-cyclohexylphenyl)propionate
ethyl α-chloro-β-(3-iodo-5-nitro-4-cyclohexylphenyl)propionate
ethyl α-chloro-β-(3-methylsulfonyl-5-nitro-4-cyclohexylphenyl)propionate
ethyl α-chloro-β-(3-trifluoromethyl-5-methylsulfonyl-4-cyclohexylphenyl)propionate
ethyl α-chloro-β-(3-nitro-5-methylsulfonyl-4-cyclohexylphenyl)propionate
ethyl α-chloro-β-(3-bromo-5-methylsulfonyl-4-cyclohexylphenyl)propionate
ethyl α-chloro-β-(3-chloro-5-methylsulfonyl-4-cyclohexylphenyl)propionate
ethyl α-chloro-β-(3-methylsulfonyl-4-cyclohexylphenyl)propionate
ethyl α-chloro-β-(3-iodo-4-cyclohexylphenyl)propionate
ethyl α-chloro-β-(3-chloro-5-iodo-4-cyclohexylphenyl)propionate
ethyl α-chloro-β-(3-iodo-5-fluoro-4-cyclohexylphenyl)propionate
ethyl α-chloro-β-(3-iodo-5-bromo-4-cyclohexylphenyl)propionate
ethyl α-chloro-β-(3-iodo-5-methylsulfonyl-4-cyclohexylphenyl)propionate

EXAMPLE 4

α-Chloro-β-(3-chloro-4-cyclohexylphenyl)propionic acid

A mixture of 54.8 g. (0.167 moles) of the ethyl α-chloro-β-(3-chloro-4-cyclohexylphenyl)propionate and 160 ml. of glacial acetic acid containing 40 ml. of 37% hydrochloric acid is refluxed for 20 hours. The mixture is concentrated under reduced pressure to give a gummy residue. The latter material is dissolved in 300 ml. of n-hexane, washed with ice-cold water (100 ml. total), dried over sodium sulfate and filtered. The hexane is removed to give α-chloro-β-(3-chloro-4-cyclohexylphenyl)propionic acid.

EXAMPLE 5

When the procedures of Example 4 are followed but ethyl α-chloro-β-(3-chloro-4-cyclohexylphenyl)propionate is replaced by the dl, d and l α-chloropropionates of this invention, then the corresponding dl, d and l α-chloropropionic acids are prepared. A representative list of the products obtained are shown in Table I, below.

TABLE I

α-chloro-β-(3,5-ditrifluoromethyl-4-cyclohexylphenyl)propionic acid
α-chloro-β-(3-cyano-4-cyclohexylphenyl)propionic acid
α-chloro-β-(3-cyano-4-cyclohexylphenyl)propionic acid
α-chloro-β-(3-trifluoromethyl-4-cyclohexylphenyl)-propionic acid
α-chloro-β-(3-fluoro-4-cyclohexylphenyl)propionic acid
α-chloro-β-(4-bromo-4-cyclohexylphenyl)propionic acid
α-chloro-β-(3-nitro-5-fluoro-4-cyclohexylphenyl)-propionic acid
α-chloro-β-(3-chloro-5-nitro-4-cyclohexylphenyl)-propionic acid
α-chloro-β-(3-nitro-5-bromo-4-cyclohexylphenyl)-propionic acid
α-chloro-β-(3-nitro-5-trifluoromethyl-4-cyclohexylphenyl)propionic acid
α-chloro-β-(3-chloro-5-cyano-4-cyclohexylphenyl)-propionic acid
α-chloro-β-(3-chloro-5-cyano-4-cyclohexylphenyl)-propionic acid
α-chloro-β-(3-chloro-5-fluoro-4-cyclohexylphenyl)-propionic acid
α-chloro-β-(3-chloro-5-trifluoromethyl-4-cyclohexylphenyl)propionic acid
α-chloro-β-(3-chloro-5-methylsulfonyl-4-cyclohexylphenyl)propionic acid
α-chloro-β-(3-chloro-5-iodo-4-cyclohexylphenyl)-propionic acid
α-chloro-β-(3-chloro-5-fluoro-4-cyclohexylphenyl)-propionic acid
α-chloro-β-(3-chloro-5-bromo-4-cyclohexylphenyl)-propionic acid
α-chloro-β-(3,5-difluoro-4-cyclohexylphenyl)propionic acid
α-chloro-β-(3-cyano-5-fluoro-4-cyclohexylphenyl)-propionic acid
α-chloro-β-(3-cyano-5-fluoro-4-cyclohexylphenyl)-propionic acid
α-chloro-β-(3-bromo-5-fluoro-4-cyclohexylphenyl)-propionic acid
α-chloro-β-(3-cyano-5-bromo-4-cyclohexylphenyl)-propionic acid
α-chloro-β-(3,5-dibromo-4-cyclohexylphenyl)propionic acid
α-chloro-β-(3-fluoro-5-trifluoromethyl-4-cyclohexylphenyl)propionic acid
α-chloro-β-(3-cyano-5-trifluoromethyl-4-cyclohexylphenyl)propionic acid
α-chloro-β-(3-bromo-5-trifluoromethyl-4-cyclohexylphenyl)propionic acid
α-chloro-β-(3,5-ditrifluoromethyl-4-cyclohexylphenyl)propionic acid
α-chloro-β-(3-chloro-4-cyclohexylphenyl)propionic acid
α-chloro-β-(3,5-dichloro-4-cyclohexylphenyl)propionic acid
α-chloro-β-(3-iodo-5-nitro-4-cyclohexylphenyl)propionic acid α-chloro-β-(3-methylsulfonyl-5-nitro-4-cyclohexylphenyl)propionic acid
α-chloro-β-(3-trifluoromethyl-5-methylsulfonyl-4-cyclohexylphenyl)propionic acid
α-chloro-β-(3-nitro-5-methylsulfonyl-4-cyclohexylphenyl)propionic acid
α-chloro-β-(3-bromo-5-methylsulfonyl-4-cyclohexylphenyl)propionic acid
α-chloro-β-(3-chloro-5-methylsulfonyl-4-cyclohexylphenyl)propionic acid
α-chloro-β-(3-methylsulfonyl-4-cyclohexylphenyl)propionic acid
α-chloro-β-(3-iodo-4-cyclohexylphenyl)propionic acid
α-chloro-β-(3-chloro-5-iodo-4-cyclohexylphenyl)propionic acid
α-chloro-β-(3-iodo-5-fluoro-4-cyclohexylphenyl)propionic acid
α-chloro-β-(3-iodo-5-bromo-4-cyclohexylphenyl)propionic acid
α-chloro-β-(3-iodo-5-methylsulfonyl-4-cyclohexylphenyl)propionic acid

EXAMPLE 6

α-Chloro-β-(3-chloro-4-cyclohexylphenyl)propionic acid, sodium salt

A solution of 12.4 g. of sodium bicarbonate in 135 ml. of water is added dropwise to a stirred solution of 49.3 g. (0.164 moles) of α-chloro-β-(3-chloro-4-cyclohexylphenyl)propionic acid in 150 cc. of methanol. The solvent is removed in vacuo and the residue is dried by repeated distillations with anhydrous ethanol. The crystalline residue is triturated with ether (100 cc.), collected on a filter, and washed with ether. Drying in a vacuum desiccator affords α-chloro-β-(3-chloro-4-cyclohexylphenyl)propionic acid, sodium salt.

When an equimolar amount of sodium bicarbonate in the above reaction is replaced by the compounds of Table I below, then the corresponding salt of Table II below is prepared.

TABLE I sodium hydroxide
potassium hydroxide
calcium hydroxide
potassium carbonate
magnesium bicarbonate

TABLE II

α-chloro-β-(3-chloro-4-cyclohexylphenyl)propionic acid, sodium salt
α-chloro-β-(3-chloro-4-cyclohexylphenyl)propionic acid, potassium salt
α-chloro-β-(3-chloro-4-cyclohexylphenyl)propionic acid, calcium salt
α-chloro-β-(3-chloro-4-cyclohexylphenyl)propionic acid, magnesium salt When α-chloro-β-(3-chloro-4-cyclohexylphenyl)propionic acid is replaced by d α-chloro-β-(3-chloro-4-cyclohexylphenyl)propionic acid and l α-chloro-β-(3-chloro-4-cyclohexylphenyl)propionic acid, then the products prepared are:

d  α-chloro-β(3-chloro-4-cyclohexylphenyl)propionic acid, sodium salt
d  α-chloro-β-(3-chloro-4-cyclohexylphenyl)propionic acid, potassium salt
d  α-chloro-β-(3-chloro-4-cyclohexylphenyl)propionic acid, calcium salt
d  α-chloro-β-(3-chloro-4-cyclohexylphenyl)propionic acid, magnesium salt
l  α-chloro-β-(3-chloro-4-cyclohexylphenyl)propionic acid, sodium salt
l  α-chloro-β-(3-chloro-4-cyclohexylphenylpropionic acid, potassium salt
l  α-chloro-β-(3-chloro-4-cyclohexylphenyl)propionic acid, calcium salt When the dl, d and l α-chloropropionic acid compounds of this invention are used in the above reaction, then the corresponding salt is prepared.

EXAMPLE 7

α-Chloro-β-(3-chloro-4-cyclohexylphenyl)propionic acid, diethylammonium salt

Anhydrous diethylamine (0.11 moles) is added dropwise to a stirred solution of α-chloro-β-(3-chloro-4-cyclohexylphenyl)propionic acid (0.10 moles) in 100 ml. of n-hexane at 0°C. The precipitate is collected on a filter, washed with n-hexane, and dried in a vacuum desiccator to obtain α-chloro-β-(3-chloro-4-cyclohexylphenyl(propionic acid, diethylammonium salt.

When diethylamine in the above reaction is replaced by an equimolar amount of the compounds of Table I, below, then the corresponding product of Table II, below is prepared.

TABLE I dimethylamine
β-hydroxyethylamine
piperazine
piperidine
α-methylbenzylamine
cyclohexylamine
triethylamine
phenethylamine

TABLE II

α-chloro-β-(3-chloro-4-cyclohexylphenyl)propionic acid, dimethylammonium salt
α-chloro-β-(3-chloro-4-cyclohexylphenyl)propionic acid, β-hydroxyethylammonium salt
α-chloro-β-(3-chloro-4-cyclohexylphenyl)propionic acid, triethylammonium salt
α-chloro-β-(3-chloro-4-cyclohexylphenyl)propionic acid, phenethylammonium salt

EXAMPLE 8

Ethyl α-bromo-β-(3-chloro-4-cyclohexylphenyl)propionate

To 15.6 g. (0.0476 moles) of ethyl β-(3-chloro-4-cyclohexylphenyl)lactate there is added slowly with stirring at 40°–50°C 23 g. (0.053 moles) of phosphorus pentabromide. The mixture is stirred at room temperature for 16 hours, then diluted with 70 ml. of petroleum ether, and poured into 125 ml. of ice-cold water. The organic phase is separated, washed with saturated aqueous sodium hydrogen carbonate solution, dried over anhydrous sodium sulfate, filtered and the solvent removed in vacuo to obtain ethyl α-bromo-β-(3-chloro-4-cyclohexylphenyl)propionate.

When ethyl β-(3-chloro-4-cyclohexylphenyl)lactate in the above procedure is replaced by d ethyl β-(3-chloro-4-cyclohexylphenyl)lactate or l ethyl β-(3-chloro-4-cyclohexylphenyl)lactate, then the products prepared are d ethyl α-bromo-β-(3-chloro-4-cyclohexylphenyl)propionate or l ethyl α-bromo-β-(3-chloro-4-cyclohexylphenyl)propionate.

When the above procedure is followed using the various lactates of this invention, then the corresponding α-bromopropionates are prepared.

EXAMPLE 9

When the α-bromopropionates of Example 8 are hydrolyzed according to the procedures of Examples 4 and 5, then the corresponding dl, d and l α-bromo-β-(3-chloro-4-cyclohexylphenyl)propionic acid compounds and the various α-bromopropionic acids are prepared.

EXAMPLE 10

When the α-bromopropionic acid compounds are reacted according to the procedures of Examples 6 and 7, then the corresponding α-bromopropionic acid salts are prepared.

EXAMPLE 11

Ethyl α-fluoro-β-(3-chloro-4-cyclohexylphenyl)propionate

A mixture of 123 g. (0.33 moles) of ethyl α-bromo-β-(3-chloro-4-cyclohexylphenyl)propionate is vigorously stirred at 130°–140°C with 29 g. (0.5 moles) of potassium fluoride in 100 ml. of ethylene glycol for 12 hours. The reaction mixture is cooled and 400 ml. of water is added and the crude product separates. The aqueous glycol mixture is extracted with ether, the ether is then dried, evaporated to dryness and upon distillation results in ethyl α-fluoro-β-(3-chloro-4-cyclohexylphenyl)propionate.

When ethyl α-bromo-β-(3-chloro-4-cyclohexylphenyl)propionate in the above procedure is replaced by d ethyl α-bromo-β-(3-chloro-4-cyclohexylphenyl)propionate or l ethyl α-bromo-β-(3-chloro-4-cyclohexylphenyl)propionate, then the products prepared are d ethyl α-fluoro-β-(3-chloro-4-cyclohexylphenyl)propionate or l ethyl α-fluoro-β-(3-chloro-4-cyclohexylphenyl)propionate.

When the above procedure is followed using the various α-bromo-propionates and α-bromopropionamides of this invention, then the corresponding α-fluoropropionates are prepared.

EXAMPLE 12

When the α-fluoropropionates of Example 11 are hydrolyzed according to the procedures of Examples 4 and 5, then the corresponding α-fluoro-β-(3-chloro-4-cyclohexylphenyl)propionic acid compounds and the various α-fluoropropionic acids are prepared.

EXAMPLE 13

When the α-fluoropropionic acid compounds are reacted according to the procedures of Exampels 6 and 7, then the corresponding α-fluoropropionic acid salts are prepared.

EXAMPLE 14

Ethyl α-iodo-β-(3-chloro-4-cyclohexylphenyl)propionate

A mixture of 37.3 g. (0.1 moles) of ethyl α-bromo-β-(3-chloro-4-cyclohexylphenyl)propionate and 150 g. of sodium iodide in 1 liter of anhydrous acetone is refluxed for 4 hours. The reaction mixture is then evaporated to dryness and extracted with ether. The ether is then washed with water, dried and evaporated to dryness to obtain ethyl α-iodo-β-(3-chloro-4-cyclohexylphenyl)propionate.

When ethyl α-bromo-β-(3-chloro-4-cyclohexylphenyl)propionate in the above procedure is replaced by d ethyl α-bromo-β-(3-chloro-4-cyclohexylphenyl)propionate or l ethyl α-bromo-β-(3-bromo-4-cyclohexylphenyl)propionate, then the products prepared are d ethyl α-iodo-β-(3-chloro-4-cyclohexylphenyl)propionate or l ethyl α-iodo-β-(3-chloro-4-cyclohexylphenyl)propionate.

When the above procedure is followed using the various α-bromopropionates of this invention, then the corresponding α-iodopropionates are prepared.

EXAMPLE 15

When the α-iodopropionates of Example 14 are hydrolyzed according to the procedures of Examples 4 and 5, then the corresponding α-iodo-β-(3-chloro-4-cyclohexylphenyl)propionic acid compounds and the various α-iodopropionic acids are prepared.

EXAMPLE 16

When the α-iodopropionic acid compounds are reacted according to the procedures of Examples 6 and 7, then the corresponding α-iodopropionic acid salts are prepared.

U.S. Pat. No. 3,860,624 describes in detail the preparation of the starting materials for producing the compounds according to the present invention as well as in general the preparation of substituted p-cycloalkylphenyl alkanoic acid compounds including the compounds of the present invention, their compounding to useful pharmaceutical preparations, and their administration in therapy, dosage, and the like.

I claim:
1. A compound of the formula

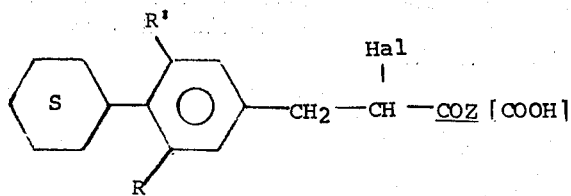

where:
R is
   chloro,
   bromo,
   nitro,
   methylsulfonyl,
   trifluoromethyl or
   cyano;
R' is
   hydrogen,
   chloro,
   bromo or
   nitro;
Hal is
   fluoro,
   chloro or
   bromo; and
Z is
   hydroxyl,
   lower alkoxy,
   phenyl lower alkoxy, or the group —OM in which M is a member of an alkali metal, alkaline earth metal, aluminum, ammonium, and di-lower alkyl ammonium.

2. A compound according to claim 1 where:
Hal is fluoro.

3. A compound according to claim 1 where:
Hal is bromo.

4. A compound according to claim 1 where:
Hal is chloro.

5. A compound according to claim 4 where:
R is trifluoromethyl and R' is hydrogen thus forming α-chloro1β-(3-trifluoromethyl-4-cyclohexylphenyl)propionic acid.

6. A compound according to claim 4 where:
R is methylsulfonyl and R' is hydrogen thus forming α-chloro-β-(3-methylsulfonyl-4-cyclohexylphenyl)propionic acid.

7. A compound according to claim 4 which is dextrorotatory.

8. A compound according to claim 4 which is levorotatory.

9. A compound according to claim 4 where:
R is bromo and R' is hydrogen thus forming α-chloro-β-(3-bromo-4-cyclohexylphenyl)propionic acid.

10. A compound according to claim 4 where:
R and R' are chloro thus forming α,3,5-trichloro-β-(4-cyclohexylphenyl) propionic acid.

11. A compound according to claim 7 where:
R and R' are chloro thus forming d α,3,5-trichloro-β-(4-cyclohexylphenyl) propionic acid.

12. A compound according to claim 8 where:
R and R' are chloro thus forming l α,3,5-trichloro-β-(4-cyclohexylphenyl) propionic acid.

13. A compound according to claim 4 where:
R is nitro and R' is hydrogen thus forming α-chloro-β-(3-nitro-4-cyclohexylphenyl)propionic acid.

14. A compound according to claim 4 where:
R is bromo and R' is chloro thus forming α,3-dichloro-β-(5-bromo-4-cyclohexylphenyl)propionic acid.

15. An α,3-dichloro-β-(4-cyclohexylphenyl) propionic acid compound of the formula

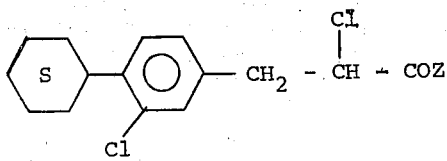

in which
Z is
 hydroxyl,
 lower alkoxy,
 phenyl lower alkoxy, or
 the group OM in which M is a member of an alkali metal, alkaline earth metal, aluminum, ammonium, and di-lower alkyl ammonium.

16. The compound of claim 15 wherein M is diethylammonium.

17. The compound of 15 wherein M is sodium.

18. The compound of claim 15 wherein Z is ethoxy.

19. α,3-Dichloro-β-(4-cyclohexylphenyl) propionic acid of the formula

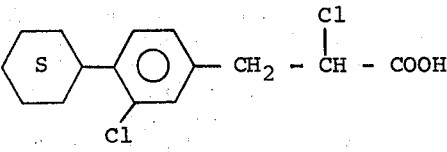

20. The dextrorotatory compound of claim 19.
21. The levorotatory compound of claim 19.

* * * * *